(12) United States Patent
Little, III et al.

(10) Patent No.: US 11,150,181 B2
(45) Date of Patent: Oct. 19, 2021

(54) METHOD FOR COMPUTING AND COMPARING DIGITAL SIGNATURES OF HYDROCARBONS

(71) Applicant: JP3 Measurement, LLC, Austin, TX (US)

(72) Inventors: Joseph Paul Little, III, Austin, TX (US); Matthew Thomas, Austin, TX (US); Gregg Williams, Driftwood, TX (US); James Stephen Dixson, III, Austin, TX (US)

(73) Assignee: JP3 Measurement, LLC, Austin, TX (US)

( * ) Notice: Subject to any disclaimer, the term of this patent is extended or adjusted under 35 U.S.C. 154(b) by 400 days.

(21) Appl. No.: 16/210,979

(22) Filed: Dec. 5, 2018

(65) Prior Publication Data
US 2019/0170641 A1    Jun. 6, 2019

Related U.S. Application Data

(60) Provisional application No. 62/594,969, filed on Dec. 5, 2017.

(51) Int. Cl.
| | |
|---|---|
| *G01N 21/359* | (2014.01) |
| *G01N 33/28* | (2006.01) |
| *G01N 21/3577* | (2014.01) |
| *G01N 21/3504* | (2014.01) |

(52) U.S. Cl.
CPC ....... *G01N 21/359* (2013.01); *G01N 33/2823* (2013.01); *G01N 21/3504* (2013.01); *G01N 21/3577* (2013.01); *G01N 2201/1293* (2013.01)

(58) Field of Classification Search
CPC ............. G01N 21/359; G01N 21/3577; G01N 33/2823
USPC .......................................................... 702/28
See application file for complete search history.

(56) References Cited

U.S. PATENT DOCUMENTS

| | | | | |
|---|---|---|---|---|
| 4,686,475 A | * | 8/1987 | Kober ................... | G01V 3/082 324/347 |
| 2003/0162224 A1 | * | 8/2003 | Chait .................... | G01N 33/68 435/7.1 |
| 2011/0306147 A1 | * | 12/2011 | Ouerdane .......... | H01J 49/0009 436/173 |
| 2013/0102066 A1 | * | 4/2013 | Bureau .............. | G01N 21/3563 435/288.7 |

(Continued)

*Primary Examiner* — Michael P Nghiem
(74) *Attorney, Agent, or Firm* — DuBois, Bryant & Campbell, LLP; William D. Wiese

(57) ABSTRACT

A system and method for encapsulating commercially significant attributes of a hydrocarbon product into a single digital signature are presented. The digital signature may be generated from a physical product sample using optical techniques such as NIR spectroscopy. Digital signatures may be expressed in the form of composition, principle components derived from the spectra, or other properties derived from the original spectra which characterize, and help visualize, the variation present within the signals. Other physical property measurements and contaminant measurements may also be included in the digital signature and may be derived from the same measurement device or separate measurement devices whose output is integrated into a single digital signature. Embodiments of the invention may be used to confirm the identity of a hydrocarbon product, or to verify the composition of a hydrocarbon product.

23 Claims, 6 Drawing Sheets

(56) References Cited

U.S. PATENT DOCUMENTS

2016/0061719 A1* 3/2016 Lambert .............. G01N 21/359
                                                        702/28
2016/0258922 A1* 9/2016 Formolo ................. E21B 49/00
2018/0321215 A1* 11/2018 Peterson ................. E21B 47/11

* cited by examiner

| PARAMETER | VALUE | T2 | Q |
|---|---|---|---|
| VPCR [PSI] | 10.84 | 0.05 | 2.8 |
| LNP [IV%] | 11.96 | 0.12 | 4.51 |
| NAP [IV%] | 22.68 | 0.15 | 5.26 |
| LET [IV%] | 27.65 | 0.17 | 4.74 |
| DSL [IV%] | 13.23 | 0.09 | 4.46 |
| GO [IV%] | 20.06 | 0.12 | 3.98 |
| RESID [IV%] | 4.38 | 0.17 | 4.72 |

| PARAMETER | OUTPUT | VALUE | T2 | Q |
|---|---|---|---|---|
| C1 [mol%] | 19.82 | 20.33 | 0.3 | 0.3 |
| C2 [mol%] | 13.39 | 13.73 | 0.29 | 0.51 |
| C3 [mol%] | 12.78 | 13.11 | 0.49 | 0.45 |
| iC4 [mol%] | 1.52 | 1.56 | 0.5 | 0.27 |
| nC4 [mol%] | 7.08 | 7.26 | 0.5 | 0.2 |
| iC4 [mol%] | 2.53 | 2.6 | 0.27 | 0.58 |
| nC5 [mol%] | 3.75 | 3.85 | 0.25 | 0.42 |
| C6 [mol%] | 3.08 | 3.16 | 0.34 | 0.55 |
| C7 [mol%] | 4.01 | 4.11 | 0.32 | 0.68 |
| C8 [mol%] | 4.07 | 4.17 | 0.33 | 0.66 |
| C9 [mol%] | 4.4 | 4.51 | 0.54 | 1.77 |
| C10 [mol%] | 3.6 | 3.69 | 0.6 | 2.2 |
| C11 [mol%] | 2.55 | 2.62 | 0.27 | 2.69 |
| C12 [mol%] | 2.55 | 2.62 | 0.27 | 2.69 |
| C13 [mol%] | 1.9 | 1.95 | 0.11 | 0.63 |
| C14 [mol%] | 1.6 | 1.64 | 0.19 | 0.67 |
| C15 [mol%] | 1.35 | 1.38 | 0.18 | 0.69 |
| C16 [mol%] | 1.14 | 1.17 | 0.21 | 0.69 |
| C17 [mol%] | 1.14 | 1.17 | 0.2 | 0.69 |
| C18 [mol%] | 1.03 | 1.06 | 0.31 | 1.08 |
| C19 [mol%] | 0.73 | 0.75 | 0.23 | 0.7 |
| C20 [mol%] | 0.86 | 0.88 | 0.86 | 1.51 |
| C21 [mol%] | 0.69 | 0.71 | 0.38 | 1.44 |
| C22 [mol%] | 0.47 | 0.48 | 0.55 | 1.96 |
| C23 [mol%] | 0.39 | 0.4 | 0.54 | 1.96 |
| C24 [mol%] | 0.33 | 0.34 | 0.56 | 1.94 |
| C25 [mol%] | 0.32 | 0.33 | 0.53 | 1.96 |

FIG. 4C

| PARAMETER | OUTPUT | VALUE | T2 | Q |
|---|---|---|---|---|
| VPCR[psi] | 9.5 | 9.51 | 0.14 | 3.38 |
| IBP[degF] | 86.1 | 86.07 | 0.33 | 1.91 |
| 5%[degF] | 172.3 | 172.34 | 0.3 | 2.46 |
| 10%[degF] | 208.6 | 208.6 | 0.31 | 2.47 |
| 20%[degF] | 268.2 | 268.22 | 0.31 | 2.47 |
| 30%[degF] | 337.7 | 337.71 | 0.34 | 2.48 |
| 40%[degF] | 416.3 | 416.26 | 0.34 | 2.48 |
| 50%[degF] | 502.9 | 502.92 | 0.35 | 2.48 |
| 60%[degF] | 594.4 | 594.44 | 0.34 | 2.48 |
| 70%[degF] | 694.9 | 694.88 | 0.33 | 2.48 |
| 80%[degF] | 817.1 | 817.15 | 0.32 | 2.48 |
| 90%[degF] | 979.7 | 979.73 | 0.32 | 2.46 |
| 95%[degF] | 1090 | 1089.98 | 0.14 | 2.12 |
| FBP[degF] | 1286.7 | 1286.68 | 0.14 | 2.12 |

FIG. 5C

METHOD FOR COMPUTING AND COMPARING DIGITAL SIGNATURES OF HYDROCARBONS

PRIORITY STATEMENT UNDER 35 U.S.C. § 119 & 37 C.F.R. § 1.78

This non-provisional application claims priority based upon prior U.S. Provisional Patent Application Ser. No. 62/594,969 filed Dec. 5, 2017, in the names of Joseph Paul Little, III, Matthew R. Thomas, Gregg Williams, and James Stephen Dixson, III entitled "METHOD FOR COMPUTING AND COMPARING DIGITAL SIGNATURES OF HYDROCARBONS," the disclosures of which are incorporated herein in their entirety by reference as if fully set forth herein.

BACKGROUND OF THE INVENTION

This invention relates to methods and systems for compositional analysis, and more particularly, to the acquisition and comparison of the hydrocarbon product data.

In current practice, crude oil from individual oil wells is transported through flow lines to individual vessels generally located at or near the well site. From there, the oil may undergo further separation, treating, heating, dehydrating, compressing, blending, pumping or other processing activities before being transported downstream, via truck, pipeline, rail car or other transportation method. It can enter into gathering lines to a point where it enters a common carrier pipeline and eventually arrives at the refinery. When custody of oil is transferred from one owner or processing point to another during this process, it is useful to know the composition and physical properties of the oil being transferred for a variety of reasons, including, but not limited to, the sale price of the crude, the desired final destination for refining, and the timing of the delivery, safety and material handling requirements for storage/transportation.

The current standard for assessing the "quality" of oil in the field is determining its relative density or API gravity, vapor pressure, water content, and basic solids and water content ("BS&W"). For example, upper limits may be set on the BS&W content and vapor pressure; and, the pricing of the oil is generally related to the API gravity number. In the past, oil produced from conventionally drilled wells with certain API numbers would generally all have similar compositional values. However, this general correlation is increasingly being challenged. One of the biggest contributing factors challenging this historical assumption is new production from unconventional shale formations. This shale crude oil tends to be much lighter (higher API gravity number) and can vary significantly in composition from well to well, and even from within an individual well. The amount of time the crude is stored in a tank can also have an effect on the composition. As the crude sits, it becomes "weathered", meaning some of the lighter components have flashed off and been vented, flared, or injected into the gas phase pipeline leaving the production facility. The increasing and changing sources of production have also resulted in the comingling of various streams from different sources to generate oil with specific desired properties, resulting in much different hydrocarbon compositions of blended oil than previously seen.

It would be useful to know the constituent compositions of the oil entering the common carrier line from each gathering line in real time so that the composition of the oil in the common carrier line can be monitored and adjusted as desired to meet specifications such as those imposed by individual refineries. This would enable the prevention of practices such as "bar-bell-ing" where a specified API gravity number is obtained through the combination of light end hydrocarbons with much heavier "sludge" hydrocarbons without the highly desirable intermediates such as C7-C12. The intermediate cuts are typically the transportation fuels such as, gasoline, jet fuel, and diesel which command a premium price in the marketplace. It would also allow for blending and marketing of very specific oil compositions to take place even upstream or midstream, well before selling to the refineries. Finally, it would allow the refineries to significantly increase their production efficiency and thus profit margins by monitoring incoming oil composition and paying more or less for specific blends, rather than just relying on API gravity numbers.

Therefore, there is a need presently in the marketplace wherein, for example, a purchaser wants to by a hydrocarbon product having specific compositional properties but the purchaser does not have access to methods or systems capable of acquiring the hydrocarbon properties and comparing those properties to the desired properties until long after the product has been purchased. In addition, there is a need, therefore, for a method and system for determining the energy content, refined yields, physical properties and the constituent composition of crude oil entering the common carrier lines or other transportation systems such as rail cars or trucks from each gathering line, or passing through custody transfer points, in real time so that the composition of the oil can be monitored and adjusted as desired.

SUMMARY OF THE INVENTION

Embodiments of the present invention provide a system and method for eliminating the problems associated with previous hydrocarbon product identification techniques by providing a method of encapsulating all of the commercially significant attributes of the product into a single digital signature. This digital signature may be a "digital crude signature" or "digital gas signature," and can be generated from a physical product sample using previously described optical techniques, including but not limited to NIR spectroscopy.

This signature may be expressed in the form of composition, such as, for example, C1-C30+ components, total boiling point cuts (e.g., light ends, gasoline, etc.), simulated distillation cuts (e.g., IBP 5%, 10%, etc.), principle components derived from the spectra, or other properties derived from the original spectra which characterize, and help visualize, the variation present within the signals. Other physical property measurements, such as, for example, RVP, and contaminant measurements, such as, for example, total sulphur or basic sediment and water, may also be included in the digital signature and may be derived from the same measurement device or separate measurement devices whose output is integrated into a single digital signature.

Various embodiments of the invention may be used to assert two measurements of the same batch of a hydrocarbon product are exactly the same. This could be used to detect, for example, dilution of the product or to confirm origin and chain of custody of the product.

Alternatively, embodiments of the present invention may be used to assert compliance of a batch of a hydrocarbon product with a contractual set of compositional requirements. For example, if the contract requires a composition having X percentage of C9, the digital signature of a sample may be compared with the digital signature of the compositional requirement to confirm compliance. This could be used, for example, as the inspection criteria on a blockchain-enabled transaction.

The foregoing has outlined rather broadly certain aspects of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 4C is a table showing the mole percentages of the hydrocarbons in the hydrocarbon product of FIG. 4A;

FIG. 5C is a table showing the mole percentages of the hydrocarbons in the hydrocarbon product of FIG. 5A;

DESCRIPTION OF THE PREFERRED EMBODIMENTS

Figure 1:
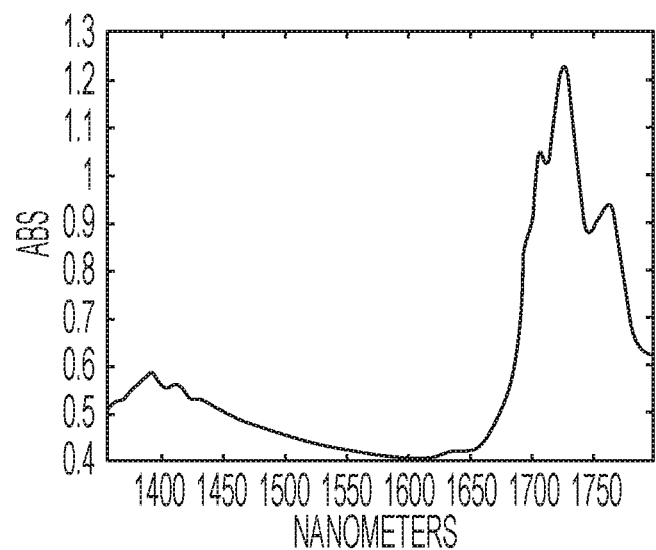
FIG. 1 depicts an absorption spectra of a crude taken with a near infrared spectrometer.

The present invention is directed to improved methods and systems for, among other things, compositional analysis and comparison of hydrocarbons. The configuration and use of the presently preferred embodiments are discussed in detail below. It should be appreciated, however, that the present invention provides many applicable inventive concepts that can be embodied in a wide variety of contexts other than comparing a single hydrocarbon product with another. Accordingly, the specific embodiments discussed are merely illustrative of specific ways to make and use the invention, and do not limit the scope of the invention. In addition, the following terms shall have the associated meaning when used herein:

"fluid infrastructure" means any infrastructure used in connection with the collection, processing, storage, transmission or distribution of a fluid including, without limitation, if the fluid is a hydrocarbon, any infrastructure between the wellhead and the point of retail delivery; and "hydrocarbon product" means any hydrocarbon gas or liquid, including but not limited to natural gas, natural gas liquids (NGL), or crude oil.

Embodiments of the present invention involve the collection, analysis and comparison of hydrocarbon products throughout a fluid infrastructure to provide a unique digital signature that can be referenced from or embedded into transactions as a digital signature. This digital signature will enable the tracking of each batch of crude from purchase through onload, transport, inspection, batch separation and blending, and offload scenarios to ensure that the hydrocarbon product purchased is the same as the hydrocarbon product that is delivered, and to eliminate, for example, unauthorized blending, dilution via addition of water or lower-value condensate, or accidental mis-delivery of shipments.

The novel aspects of various embodiments of the invention described herein represent an industry transforming indicator of the quality and value of crude oil. The use of digital signatures replaces the use of the traditional single API gravity number with a robust set of data that is a much more comprehensive and definitive indicator of the characteristics of the hydrocarbon product.

A digital signature is comprised of a set of physical and compositional properties which can be generated in the field at any location in the fluid infrastructure. In addition to information generated through the NIR spectra, the digital signature may be augmented or supplemented with information from other sources, such as basic sediment & water (BS&W), carbon dioxide, hydrogen sulfide, total sulfur, metal composition, micro carbon, viscosity, density and API gravity, and may also include a much higher value set of data that includes refined value properties, such as refined cuts, true boiling point curves, vapor pressure and K factor. In addition, in some embodiments the digital signature contains an eight hundred and eighty-one point NIR spectra which is unique to the compositional make-up of the hydrocarbon product being measured.

In practice, these spectra may be used in a variety of applications. For example, the spectra may be measured and compared at many points across the crude production and transportation supply chain to verify the authenticity of the hydrocarbon product that was bought, shipped and received are one and the same. In other applications, embodiments of the present invention may be used to capture other properties of interest, such as sulphur content and metals, which may be imbedded into the digital signature.

In some embodiments of the present invention, it may be desirable to use a blockchain based node and system for integration of digital signature into the fluid infrastructure. In other embodiments, the digital signatures of the present invention may be used in a data as a service (DaaS) to provide secure, real-time and historical visualization of hydrocarbon product data. The platform may be accessible from both web-based and mobile applications.

Referring now to FIG. 1, as discussed above, digital signatures of the present invention may be "digital crude signatures" or "digital gas signatures," and may be generated from a physical product sample using previously described optical techniques, including but not limited to NIR spectroscopy. One example of such an optical technique would be an absorption spectra generated by a swept source spectrometer taken at a resolution of up to 0.1 nm such as that shown in FIG. 1. The spectra is the result of transmitting a portion of the near infrared spectrum though crude and comparing it to the raw signal of the spectrometer. The interaction of the light with the compositional makeup of the crude results in the absorption spectra presented in FIG. 1. The scan range could be, for example, from 1250 nm to 2100 nm. Alternatively, a digital signature of a hydrocarbon product may be generated by specifying the desired compositional characteristics of the product.

Figure 2:
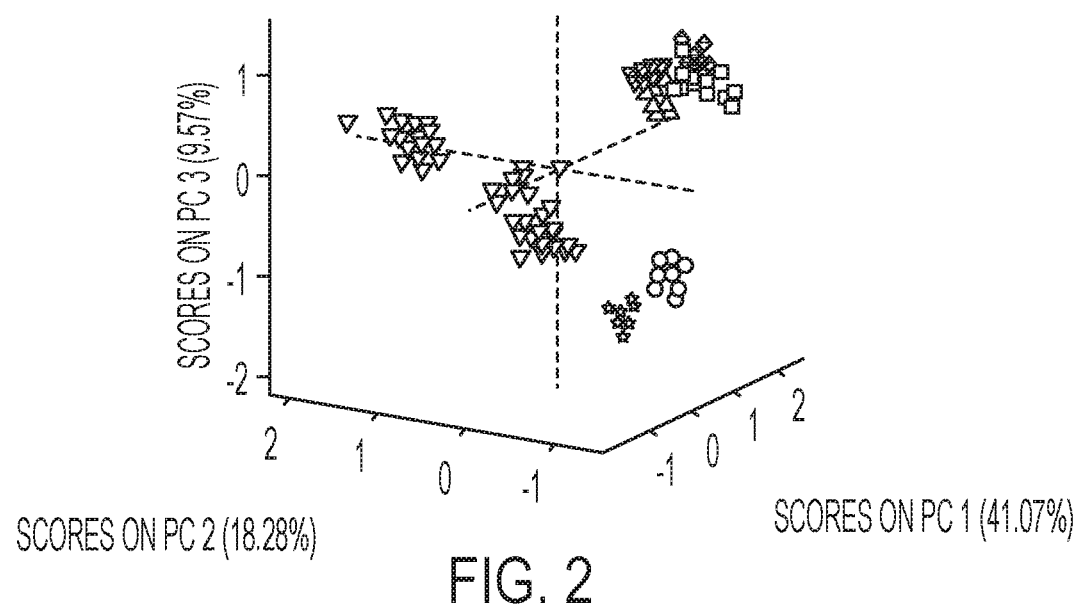
FIG. 2 depicts a spectra created from near infrared spectroscopy expressed as its principle components.

FIG. 2 is an example data from a spectra expressed as its principle components where PC 1, PC 2 and PC 3 are eigenvalues showing changes in the spectra. A hydrocarbon's principle components capture and describe the variability resident within the spectra itself. Each principle component is orthogonal to the preceding component and the components can be plotted against one another to visually express the unique attributes—or digital signature—of various spectra. The principle components can be used to describe properties of the crude, such as, for example, distillate product yields, vapor pressure, % of specific carbon numbers, polycyclic aromatics, boiling point distribution as a function temperature, sulfur content, total acid number, viscosity, relative density and water content.

For example, in some applications, various embodiments of the invention may be implemented by generating an absorption spectra using near infrared spectrometry for a batch of hydrocarbon product at a first location, such as a well head, and deconvoluting the spectra into its principle components to create a first digital signature. The principle components could be plotted, such as the plot shown in FIG. 2, to provide a graphical representation of the digital signature. A second absorption spectra of the hydrocarbon product could be generated at a second location, such as a transfer point or a point of sale, and the spectra could be deconvoluted into its principle components to create a second digital signature. The second digital signature could then be compared to the first digital signature to verify the identity, or chain of title, of the hydrocarbon product.

Figures 3A, 3B:
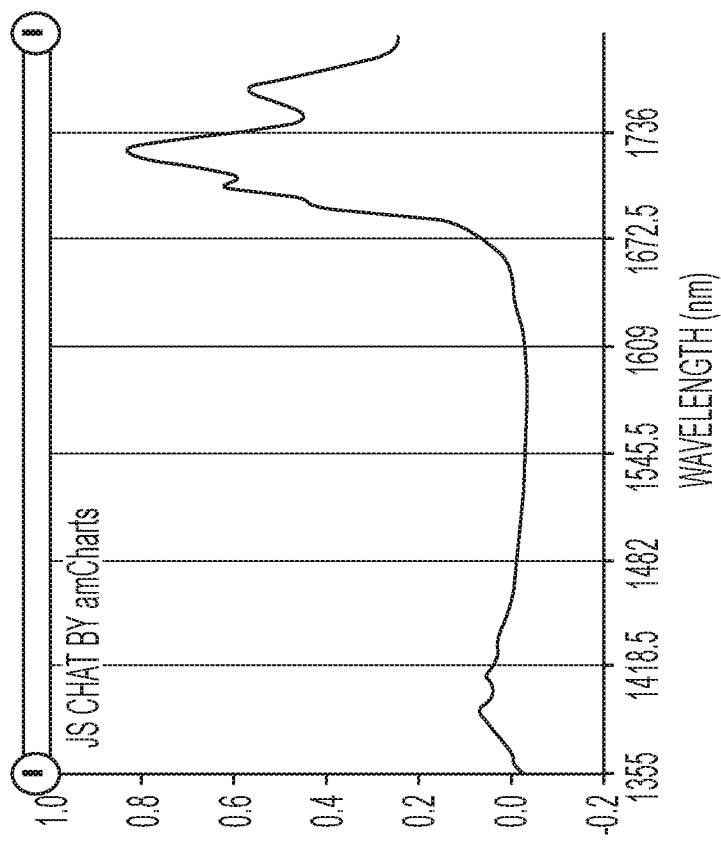
FIGS. 3A and 3B depict a raw spectra and the vapor pressure and distillate products that can be refined from a hydrocarbon product once it is processed.

FIG. 3A is a spectra of a hydrocarbon product such as that refined from a crude after processing, and FIG. 3B shows the boiling point distributions of the product. The distillate and vapor pressure calculations are a result of breaking the spectra into its principle components and describing the mathematical relationship between the product yields and vapor pressure. The matrix shows each parameter and its corresponding value, along with the Euclidian distance from the center of the model, represented as $T^2$, and the amount of resident information not being utilized by the model to characterize the corresponding parameter, represented as Q.

Figure 4A:
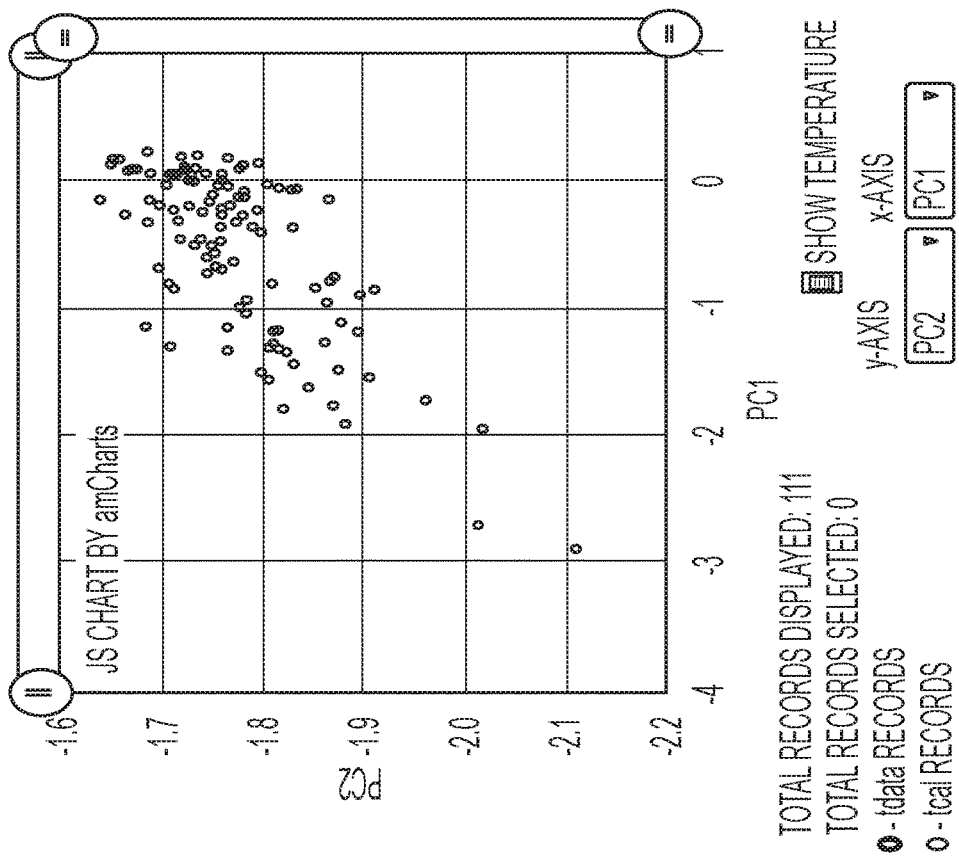
FIG. 4A depicts an exemplary spectra of a specific carbon species in a hydrocarbon product.
Figure 4B:
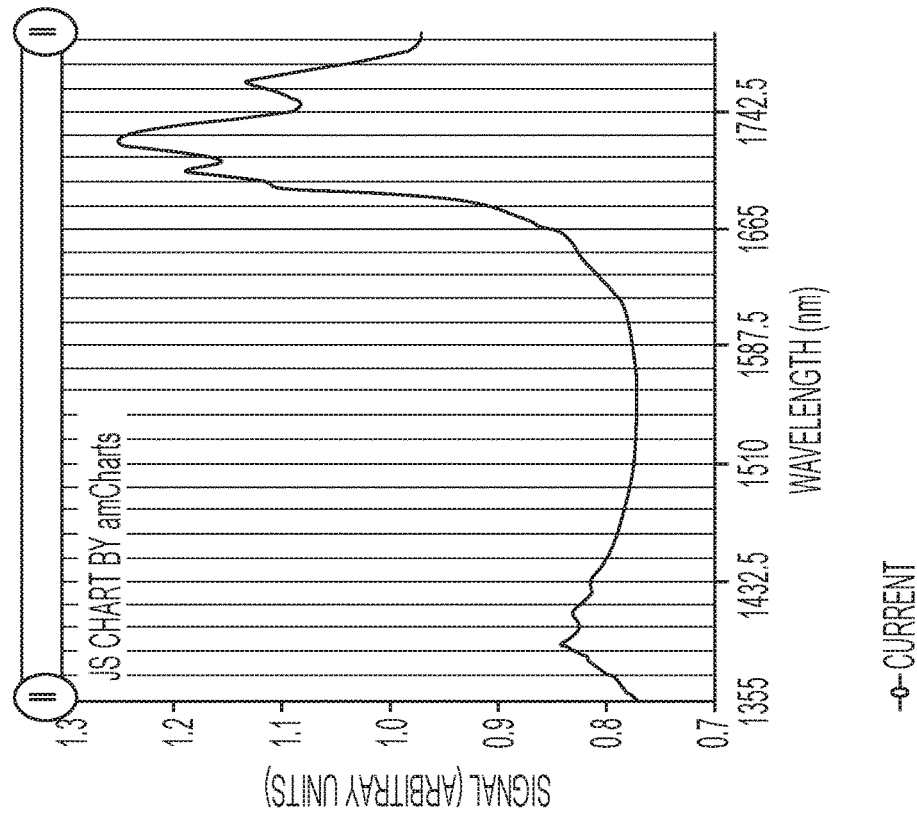
FIG. 4B depicts principle component 1 plotted against principle component 2 for a series of spectra of the hydrocarbon product of FIG. 4A.

FIG. 4A shows the raw spectra of a hydrocarbon product at a temperature of 115.4 F and a pressure of 1240 psi, FIG. 4B shows the corresponding plot of principle component 1 plotted against principle component 2, and FIG. 4C shows the corresponding mole percentage of specific carbon species in the product. The mole % calculations are a result of describing the mathematical relationship between the principle components of the spectra to the corresponding mole percentage.

Figure 5A:
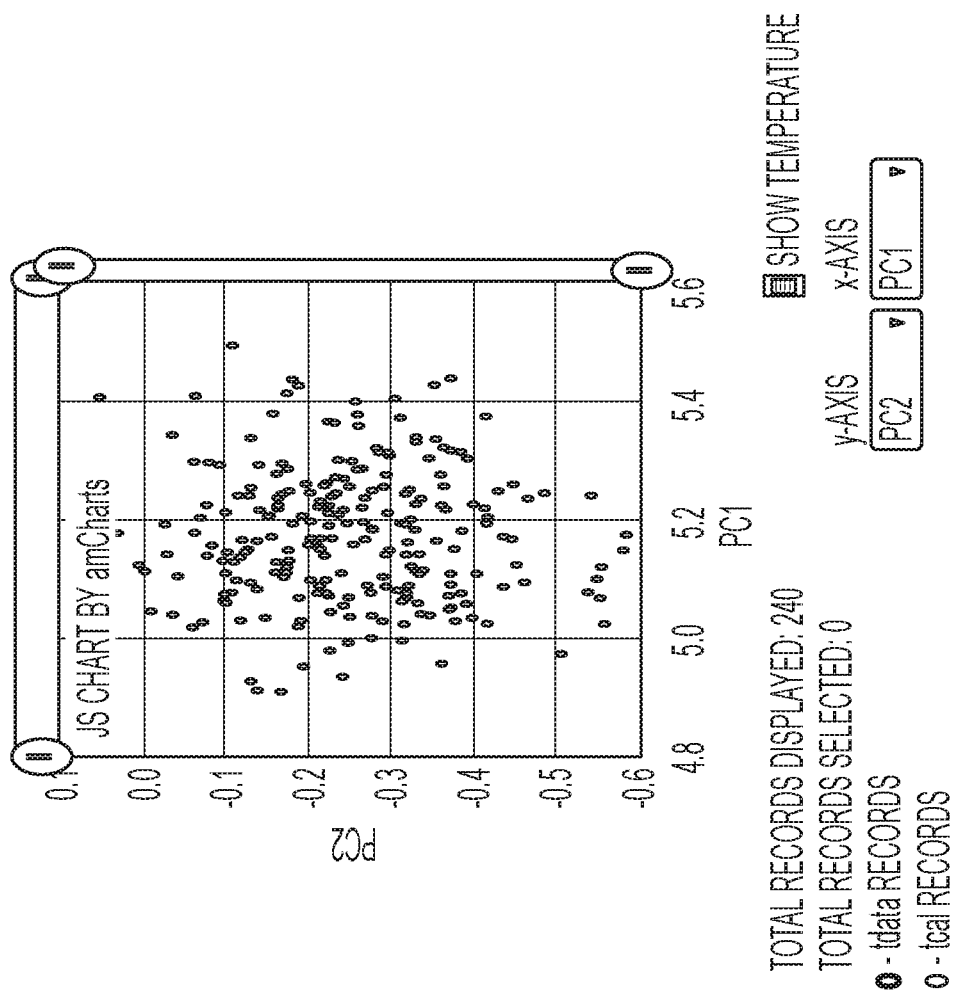
FIG. 5A depicts an exemplary spectra of a specific carbon species in a hydrocarbon product.
Figure 5B:
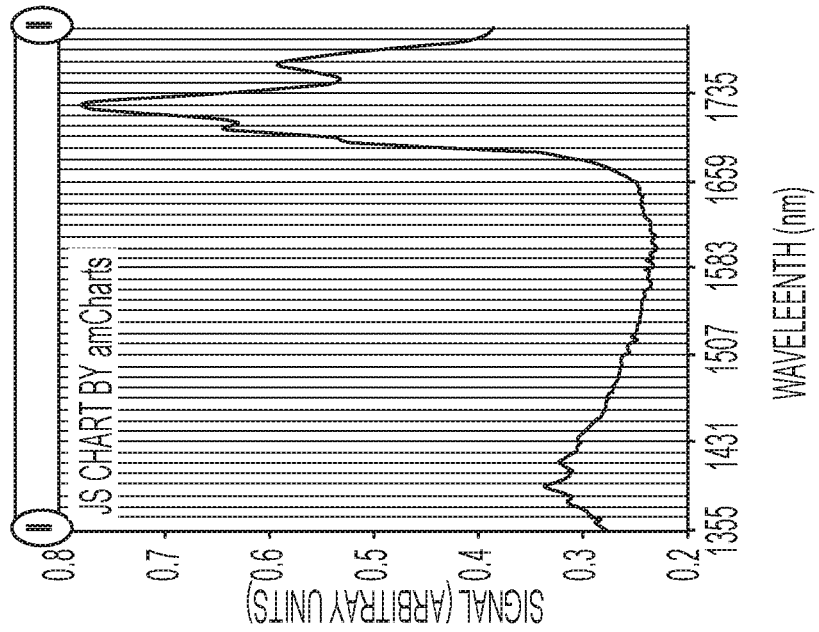
FIG. 5B depicts principle component 1 plotted against principle component 2 for a series of spectra of the hydrocarbon product of FIG. 5A.

FIG. 5A shows the raw spectra of a hydrocarbon product at a temperature of 78.8 F and a pressure of 412 psi, FIG. 5B shows a corresponding plot of principle component 1 vs principle component 2, and FIG. 5C shows the vapor pressure and the boiling point distribution as a function of temperature for the product. In addition to showing the $T^2$ and Q values as described above, the table also presents the output in degrees Fahrenheit The boil off calculations are a result of describing the mathematical relationship between the principle components of the spectra to the corresponding temperature at which a given percentage of the overall product has boiled off. The vapor pressure is calculated in a similar manner.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for hydrocarbon analysis known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

We claim:

1. A method for verifying whether properties of a second sample of hydrocarbon product are same as properties of a first sample of hydrogen product, comprising:
    generating a first absorption spectra of the first sample of a hydrocarbon product using near infrared spectrometry;
    deconvoluting the first absorption spectra into principle components to create a first digital signature, wherein the first digital signature is expressed in the form of principle components derived from a spectra, and each principle component is orthogonal to a preceding principle component;
    generating a second absorption spectra of the second sample of a hydrocarbon product using near infrared spectrometry;
    deconvoluting the second absorption spectra into principle components to create a second digital signature;
    comparing the second digital signature with the first digital signature to verify whether properties of the second sample are same as properties of the first sample.

2. The method for verifying whether properties of a second sample of hydrocarbon product are same as properties of a first sample of hydrogen product of claim 1, wherein the first digital signature is expressed in the a form of principle components derived from a spectra.

3. The method for verifying whether properties of a second sample of hydrocarbon product are same as properties of a first sample of hydrogen product of claim 1, wherein the first digital signature is expressed in a form of principle components derived from a spectra, and the principle components are eigenvalues showing changes within an absorption spectra.

4. The method for verifying whether properties of a second sample of hydrocarbon product are same as properties of a first sample of hydrogen product of claim 1, wherein the first digital signature is expressed in a form of principle components derived from a spectra, and each principle component is orthogonal to a preceding principle component and the principal components are plotted against one another to visually express unique attributes of the spectra.

5. The method for verifying whether properties of a second sample of hydrocarbon product are same as properties of a first sample of hydrogen product of claim 1, wherein the first digital signature is derived from more than one measurement device whose output is integrated into a single digital signature.

6. The method for verifying whether properties of a second sample of hydrocarbon product are same as properties of a first sample of hydrogen product of claim 1, wherein the second digital signature is derived from more than one measurement device whose output is integrated into a single digital signature.

7. The method for verifying whether properties of a second sample of hydrocarbon product are same as properties of a first sample of hydrogen product of claim 1, wherein the first digital signature is also derived from a basic sediment and water value of the first sample, and the second digital signature is also derived from a basic sediment and water value of the second sample.

8. The method for verifying whether properties of a second sample of hydrocarbon product are same as properties of a first sample of hydrogen product of claim 1, wherein the first digital signature is also derived from a carbon dioxide value of the first sample, and the second digital signature is also derived from a carbon dioxide value of the second sample.

9. The method for verifying whether properties of a second sample of hydrocarbon product are same as properties of a first sample of hydrogen product of claim 1, wherein the first digital signature is also derived from a hydrogen sulfide value of the first sample, and the second digital signature is also derived from a hydrogen sulfide value of the second sample.

10. The method for verifying whether properties of a second sample of hydrocarbon product are same as properties of a first sample of hydrogen product of claim 1, wherein the first digital signature is also derived from a total acid number value of the first sample, and the second digital signature is also derived from a total acid number value of the second sample.

11. The method for verifying whether properties of a second sample of hydrocarbon product are same as properties of a first sample of hydrogen product of claim 1, wherein the first digital signature is also derived from a total sulfur value of the first sample, and the second digital signature is also derived from a total sulfur value of the second sample.

12. The method for verifying whether properties of a second sample of hydrocarbon product are same as properties of a first sample of hydrogen product of claim 1, wherein the first digital signature is also derived from a micro carbon value of the first sample, and the second digital signature is also derived from a micro carbon value of the second sample.

13. The method for verifying whether properties of a second sample of hydrocarbon product are same as properties of a first sample of hydrogen product of claim 1, wherein the first digital signature is also derived from a viscosity value of the first sample, and the second digital signature is also derived from a viscosity value of the second sample.

14. The method for verifying whether properties of a second sample of hydrocarbon product are same as properties of a first sample of hydrogen product of claim 1, wherein the first digital signature is derived from a metal composition value of the first sample.

15. The method for verifying whether properties of a second sample of hydrocarbon product are same as properties of a first sample of hydrogen product of claim 1, wherein the first second digital signature is also derived from a metal composition value of the first sample, and the second digital signature is alse derived from a metal composition value of the second sample.

16. The method for verifying whether properties of a second sample of hydrocarbon product are same as properties of a first sample of hydrogen product of claim 1, wherein the first digital signature is also derived from a true boiling point value of the first sample, and the second digital signature is also derived from a true boiling point value of the second sample.

17. The method for verifying whether properties of a second sample of hydrocarbon product are same as properties of a first sample of hydrogen product of claim 1, wherein the first digital signature is also derived from a vapor pressure value of the first sample, and the second digital signature is also derived from a vapor pressure value of the second sample.

18. The method for verifying whether properties of a second sample of hydrocarbon product are same as properties of a first sample of hydrogen product of claim 1, wherein the first sample is taken from a hydrocarbon product at a well head and the second sample is taken from a hydrocarbon product at a transfer point in a fluid infrastructure.

19. The method for verifying whether properties of a second sample of hydrocarbon product are same as properties of a first sample of hydrogen product of claim 1, wherein the second digital signature is also compared with the first digital signature in a blockchain or other distributed ledger environment.

20. The method for verifying whether properties of a second sample of hydrocarbon product are same as properties of a first sample of hydrogen product of claim 1, wherein the second digital signature is also compared with the first digital signature to verify chain of custody.

21. The method for verifying whether properties of a second sample of hydrocarbon product are same as properties of a first sample of hydrogen product of claim 1, wherein the second digital signature is also compared with the first digital signature to verify compliance of the second sample of a hydrocarbon product with contractual requirements.

22. The method for verifying whether properties of a second sample of hydrocarbon product are same as properties of a first sample of hydrogen product of claim 1, wherein the first digital signatures are used in a data as a service platform to provide real-time visualization of hydrocarbon product data.

23. The method for verifying whether properties of a second sample of hydrogen product are same as properties of a first sample of hydrogen product of claim 1, wherein the first absorption spectra are generated by a swept source spectrometer taken at a resolution of up to 0.1 nm with a scan range between 1250 nm and 2100 nm.

\* \* \* \* \*